US007645220B2

(12) United States Patent
Hoffman et al.

(10) Patent No.: US 7,645,220 B2
(45) Date of Patent: Jan. 12, 2010

(54) PERINEOMETER WITH WIRELESS BIOFEEDBACK

(75) Inventors: Craig A. Hoffman, Waco, TX (US); Gerry M. Hoffman, Fort Worth, TX (US); Michael John England, Fort Worth, TX (US)

(73) Assignee: Anatasol, LLC, Austin, TX (US)

( * ) Notice: Subject to any disclaimer, the term of this patent is extended or adjusted under 35 U.S.C. 154(b) by 89 days.

(21) Appl. No.: 11/268,923

(22) Filed: Nov. 8, 2005

(65) Prior Publication Data

US 2006/0036188 A1  Feb. 16, 2006

(51) Int. Cl.
*A63B 71/00* (2006.01)

(52) U.S. Cl. .......................... 482/148; 606/591; 128/25

(58) Field of Classification Search ................ 482/148, 482/112–113; 600/29, 46, 410, 30, 38, 591, 600/45; 128/905, 903; 73/379.01, 379.08; 607/138

See application file for complete search history.

(56) References Cited

U.S. PATENT DOCUMENTS

| 1,928,893 | A |   | 10/1933 | Hoard |
| 2,507,858 | A |   | 5/1950 | Kegel |
| 2,763,265 | A |   | 9/1956 | Waters |
| 3,800,800 | A | * | 4/1974 | Garbe et al. .................. 607/72 |
| 3,933,147 | A |   | 1/1976 | Du Vall et al. |
| 4,048,985 | A |   | 9/1977 | Sasse |
| 4,216,783 | A |   | 8/1980 | Kaiser et al. |
| 4,396,019 | A | * | 8/1983 | Perry, Jr. ...................... 600/546 |
| 4,653,514 | A |   | 3/1987 | Shapiro |
| 4,869,258 | A | * | 9/1989 | Hetz ........................... 600/446 |
| 5,184,619 | A |   | 2/1993 | Austin |
| 5,233,987 | A |   | 8/1993 | Fabian et al. |
| 5,483,832 | A |   | 1/1996 | Pauser et al. |
| 5,554,092 | A |   | 9/1996 | Harpstead et al. |
| 5,662,699 | A |   | 9/1997 | Hamedi et al. |
| 5,674,238 | A | * | 10/1997 | Sample et al. .............. 606/192 |
| 5,733,230 | A |   | 3/1998 | Sawchuck et al. |
| 5,800,501 | A |   | 9/1998 | Sherlock |
| 5,875,778 | A | * | 3/1999 | Vroegop ..................... 607/138 |
| 5,924,984 | A |   | 7/1999 | Rao |
| 6,063,045 | A |   | 5/2000 | Wax et al. |
| 6,169,914 | B1 | * | 1/2001 | Hovland et al. ............. 600/340 |
| 6,217,529 | B1 |   | 4/2001 | Wax et al. |
| 6,526,306 | B2 | * | 2/2003 | Johnson et al. ............. 600/411 |
| 6,625,495 | B1 |   | 9/2003 | Alon et al. |
| 6,672,996 | B2 |   | 1/2004 | Ross et al. |
| 6,807,444 | B2 | * | 10/2004 | Tu et al. ..................... 600/547 |
| 6,905,471 | B2 | * | 6/2005 | Leivseth et al. ............. 600/591 |

* cited by examiner

*Primary Examiner*—Lori Baker
(74) *Attorney, Agent, or Firm*—Dennis T. Griggs; Scott T. Griggs; Griggs Bergen LLP

(57) ABSTRACT

A perineometer for home or clinical use assesses the strength of pelvic floor muscles and provides audible and visual biofeedback signals as training aids during pelvic exercises. Impedance signals proportional to vaginal contraction pressure forces are developed by a transducer sleeve that is mounted on a vaginal probe. A battery-powered RF transmitter module contained within the probe transmits wireless impedance signals to a hand-held receiver equipped with an audio-visual display monitor. The probe reacts the pelvic contraction forces and thus provides a direct tactile feedback signal that is used in combination with audible and visual feedback signals for improving the endurance and strength of pelvic floor muscles.

20 Claims, 9 Drawing Sheets

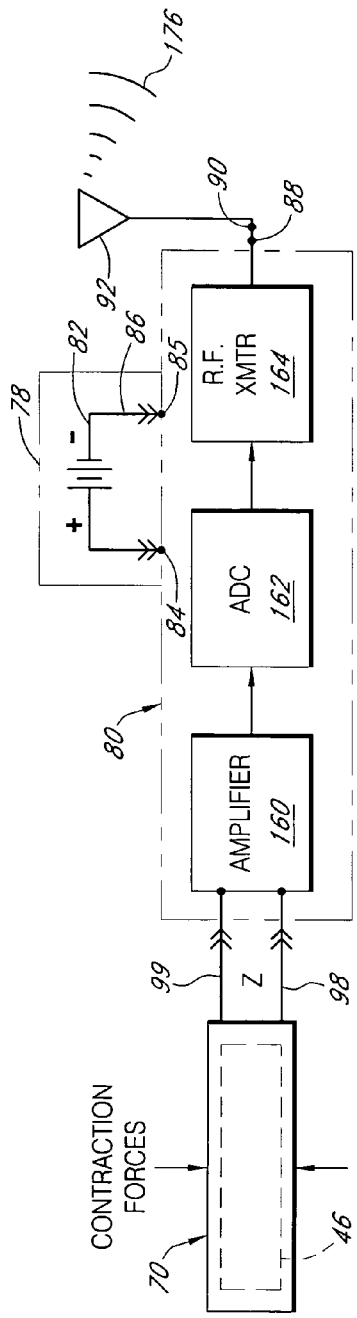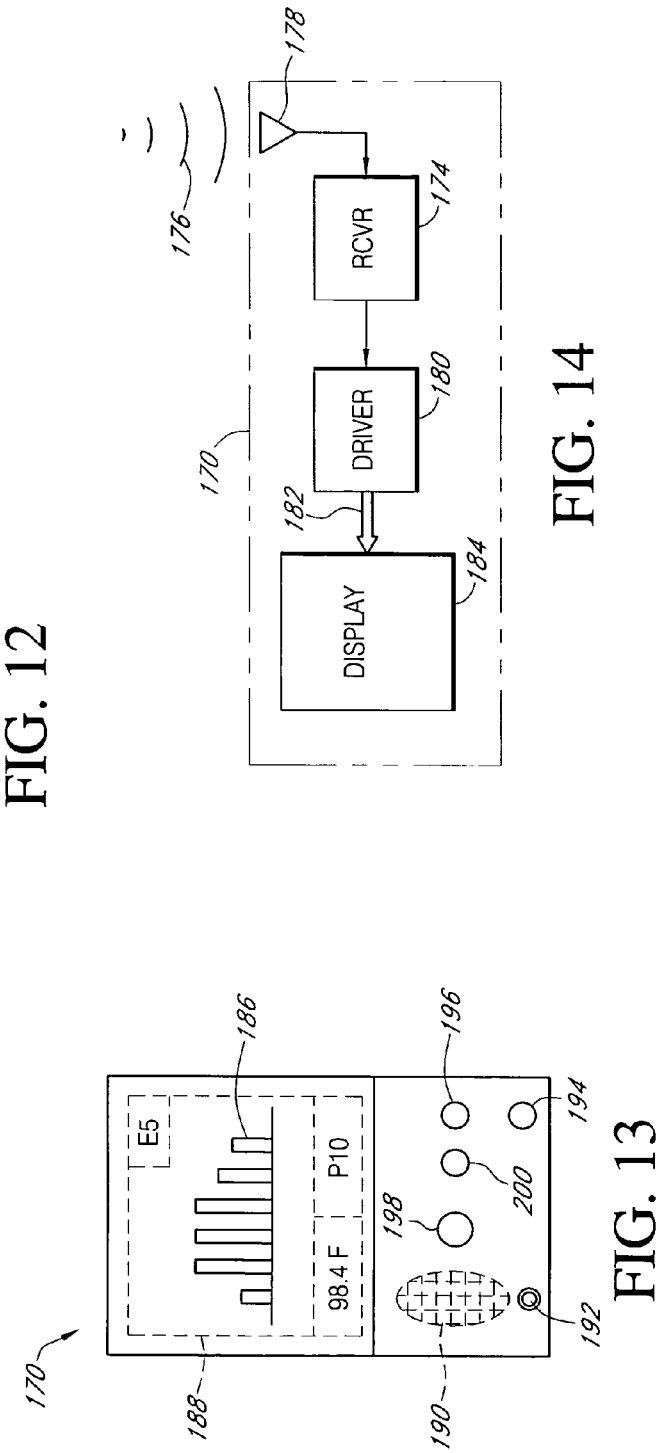
FIG. 12
FIG. 14
FIG. 13

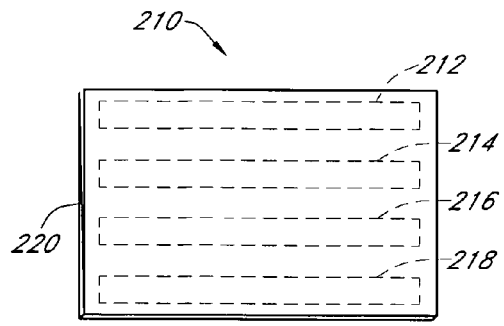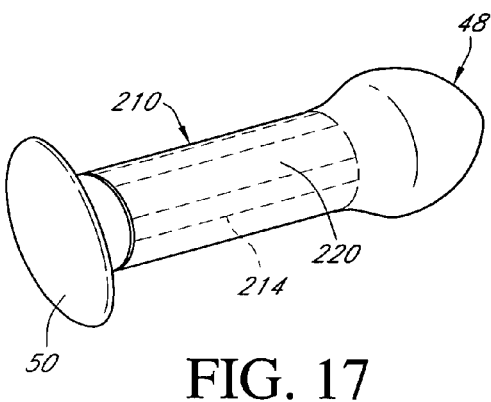
FIG. 16   FIG. 17
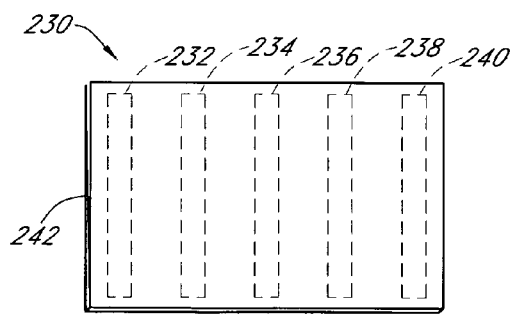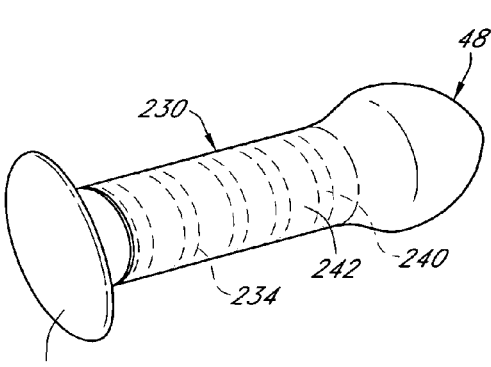
FIG. 18   FIG. 19

PERINEOMETER WITH WIRELESS BIOFEEDBACK

BACKGROUND OF THE INVENTION

1. Field of the Invention

This invention is related to exercise devices for rehabilitating and strengthening the muscles of the pelvic floor, particularly the collective group of muscles referred to as the female pubococcygeal and related perineal musculature.

2. Description of the Related Art

An area of great concern to women and health care providers as well are pelvic health disorders that involve the pelvic area (bladder, pelvic floor muscle, rectum and uterus). The lower pelvic muscles may become damaged or weakened through childbirth, lack of use, age, or as the result of surgical procedures. One of the symptoms related to a weakening of these muscles is urinary incontinence. Other pelvic disorders include chronic pelvic pain and vulvodynia (pelvic muscle dysfunction) that are sometimes experienced by young adult women. These disorders are caused by involuntary contractions (spasms) of the levator ani and perineal muscles. This condition is called vaginismus or pelvic floor tension myalgia and is accompanied by painful and difficult penetration of the vagina.

Various exercise devices have been developed in an attempt to restore the pelvic floor muscles, with the specific goal of strengthening the muscles that surround the urethra to overcome urinary incontinence in women. An early-patented pelvic exercise device is disclosed in U.S. Pat. No. 1,928,893, issued to Dr. Ralph D. Hoard in 1933. The device is intended to be inserted into a patient's vagina to exercise the vaginal muscles. It includes a two-sided tubular apparatus whose sides are biased slightly apart by springs. The sides of the tubular device are squeezed against the pressure of the springs by contraction of the vaginal muscles.

Additional patents have been issued for a number of other exercisers, including U.S. Pat. No. 2,763,265 (E. G. Waters) and U.S. Pat. No. 5,554,092 (Stanley D. Harpstead). The Waters device is a generally hard tubular probe that has varying cross sectional dimensions for assistance in identifying the various muscle groups and for applying isometric exercise to those muscle groups within or connected to the vagina. The Harpstead device is a hollow body designed to receive various configurations of weights. With the patient in the upright position, the device is inserted within the vagina so that the muscles of the vagina and the pelvic area must be constricted and held in a continuing contracted or squeezed state without further change in muscle length (isometric exercise).

U.S. Pat. No. 2,507,858 to Kegel shows an exercising device that includes a probe in the form of a pressurized sleeve that is inserted within the vagina to exercise the muscles around the vagina and to measure their strength. An external pressure gage is connected to the probe via a flexible air tube that extends externally of the vagina. The external gage provides a visual indication of muscle force applied during exercise.

Du Vall U.S. Pat. No. 3,933,147 shows a vaginal probe that includes an internal pressure sensor that is connected to an external contraction intensity meter via electrical conductors.

Perry U.S. Pat. No. 4,396,019 shows a vaginal probe equipped with electrodes for sensing minute natural electrical impulses within the vagina and communicating those impulse signals via electrical conductors to an external display unit for biofeedback purposes.

Fabian U.S. Pat. No. 5,233,987 shows a vaginal treatment probe connected to an external compliance monitor.

Pauser U.S. Pat. No. 5,483,832 shows a vaginal probe that includes an internal pressure sensor that is connected to an external display meter via electrical conductors for monitoring the contraction of pelvic floor muscles.

Wax U.S. Pat. No. 6,063,045 shows a vaginal probe that includes an internal pressure sensor that is connected to an external display device via electrical conductors for monitoring the contraction of pelvic floor muscles. Biofeedback patterns formed on the display device guide the patient through an exercise routine.

Notwithstanding the existence of such conventional exercise devices, there is a continuing interest in an improved exerciser that allows the patient to exercise the vaginal muscle groups in complete privacy at home or under clinical supervision, with dynamic real-time biofeedback, is simple to use, has a low risk of injury and is easy to maintain. There is a further need for a biofeedback probe and monitor for use by women who are experiencing painful pelvic spasms (pelvic floor tension myalgia), that provides visual as well tactile feedback signals as an aid for training pelvic muscle relaxation techniques.

SUMMARY OF THE INVENTION

The present invention provides a passive exercise device for the pelvic floor muscles, including the collective group of muscles involved in sexual response. The invention features a self-contained perineometer probe for intravaginal use that communicates a wireless biofeedback signal to a small portable receiver and display unit. The display unit provides an audible signal and visual display that allows the patient to monitor her efforts as self-directed or according to a prescribed training protocol as prompted by a pre-programmed routine contained in the display unit.

The invention in particular provides a perineometer for intravaginal use in connection with the development, training and rehabilitation of the female pubococcygeal and related perineal musculature. An impedance signal proportional to pressure forces applied during contraction of the pelvic floor muscles is developed by a pressure transducer mounted on an insertable vaginal probe. The transducer impedance signal is converted to a digital data feedback signal by a miniature electronics module contained within the probe. The digital feedback signal is communicated to an external monitor via a high frequency wireless radio frequency transmitter contained in the electronics module.

The digital data impedance signal is received and converted to a visible and/or audible signal in a hand-held monitor in real time for biofeedback training purposes. The electronics module is completely self-contained with an internal wireless RF transmitter, antenna and battery. Since the probe is worn intravaginally with minimal external reveal, it can be used in the home in complete privacy or under clinical supervision.

According to one aspect of the invention, the pressure transducer is in the form of a sleeve that is wrapped or fitted around the probe housing. The sleeve is substantially coextensive in length with the female pubococcygeal and related perineal musculature that surrounds the vaginal cavity. The sensing body of the pressure transducer is a variable resistance element that exhibits a change in electrical impedance in response to a change in the amplitude of a pressure force or mechanical stress applied to the transducer sleeve.

According to another aspect of the invention, the variable resistance element of the pressure transducer is provided by a body of an insulating or weakly conductive polymer composition containing a dispersed matrix of particles of at least one strongly conductive material selected from the group consisting of metals, alloys and reduced metal oxides. A thin layer of the weakly conductive polymer composition is sandwiched between first and second conductive electrodes, and then arranged in the form of an annular sleeve.

According to another aspect of the invention, the transducer sensing body is provided by a textile fabric sleeve assembly composed of textile form electrodes, textile form variable resistance elements and textile form conductive members arranged in the form of an annular sleeve.

According to yet another aspect of the invention, the transducer sensing body is provided by a flexible, multi-layer laminate of an outer contact layer of a non-conductive dielectric material, a middle layer of a polymeric piezoelectric material having metallized coating layers on either side thereof, and a base layer of a non-conductive dielectric material, arranged in the form of an annular sleeve.

The transducer sleeve is fitted about the external surface of the probe shaft which serves as a reaction core member. The probe shaft supports the transducer sleeve and reacts compression loading applied by the pubococcygeal and related perineal musculature during pelvic contractions. The transducer sleeve is stressed in accordance with changes in applied loading and produces a dynamic impedance output signal that changes in proportion to the pelvic contraction pressure, while the reaction forces from the core member provide direct tactile sensory feedback.

Since the probe is retained during exercise and the reaction core member is substantially coextensive with the pelvic muscles, it can be sensed or felt when the muscles are contracted against it. The exercising device of the invention encourages pelvic muscle reeducation and strengthening by (1) giving direct tactile sensory feedback to the patient during exercise which allows the patient to identify the pelvic floor muscles and confirm that the probe is properly engaged; (2) developing muscle strength and endurance due to the work required of the muscles to contract against the reaction core member, thereby creating muscle memory; and (3) giving audible and/or visual sensory feedback that is directly related to performance during exercise, thus instilling patient confidence that the device is being used properly and that the exercises are having the desired training effect.

BRIEF DESCRIPTION OF THE DRAWING FIGURES

FIG. 12 is simplified block diagram of an R.F. transmitter module that is contained within the shaft of the perineometer probe;

FIG. 13 is front elevation view of a hand-held monitor that receives RF wireless signals from the perineometer probe transmitter module and provides a visual display of the pressure waveform and audible feedback signals in response to pelvic contractions;

FIG. 14 is simplified circuit block diagram of the hand-held monitor of FIG. 13;

FIG. 16 is a developed plan view of a transducer sleeve with multiple strip form transducer elements, shown in its flat configuration prior to assembly onto the perineometer probe;

FIG. 17 is a perspective view of the strip form transducer sleeve shown assembled on a probe;

FIG. 18 is a developed plan view of a transducer sleeve with multiple band form transducer elements, shown in its flat configuration prior to assembly onto the perineometer probe;

FIG. 19 is a perspective view of the multiple band form transducer sleeve shown assembled onto a probe;

DETAILED DESCRIPTION OF THE PREFERRED EMBODIMENTS OF THE INVENTION

Figure 1:
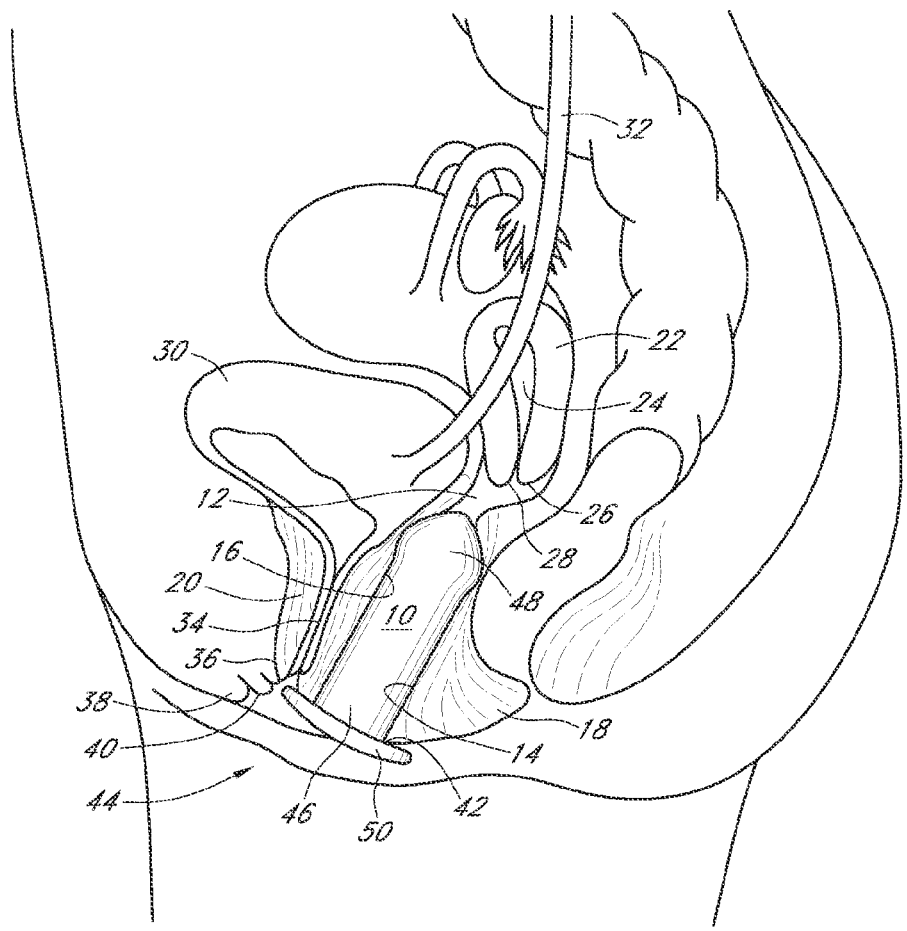
FIG. 1 is a simplified sectional view of the pelvic region of the female anatomy, showing the perineometer probe of the present invention inserted within the intravaginal cavity in the operative sensing position.
Figure 15:
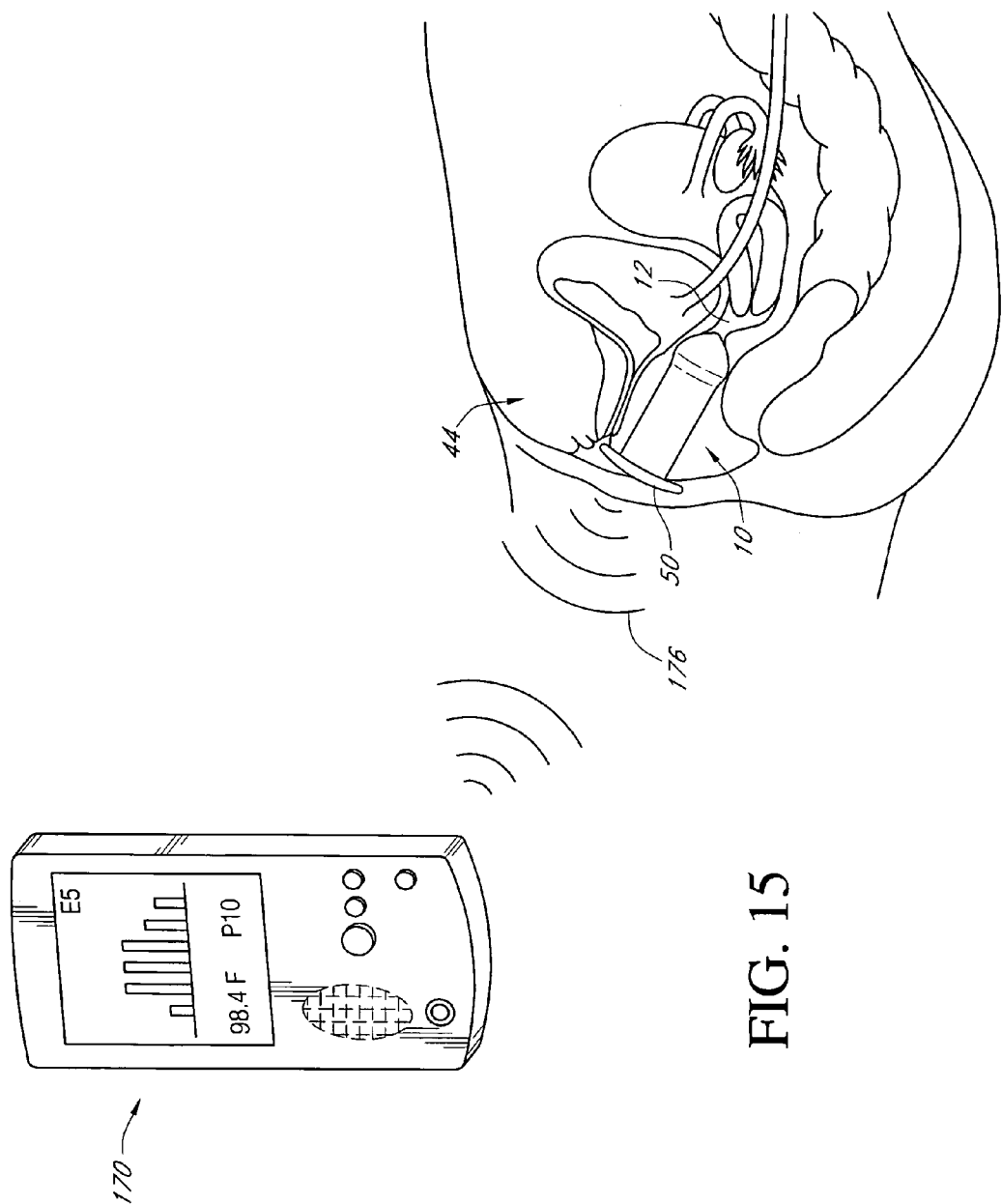
FIG. 15 is a diagram that illustrates use of the perineometer in combination with the hand-held monitor, by a patient in the preferred lithotomy position.

The specification which follows describes the preferred embodiments with reference to portions of the female pelvic anatomy that are shown in FIG. 1, and with reference to the lithotomy position indicted in FIG. 15. The perineometer probe 10 of the present invention is inserted in the vaginal cavity 12 while the patient is reclining in the slightly elevated lithotomy position. In that position, the patient is lying on her back, knees raised, with her head slightly elevated relative to the pelvic region. Her torso is on an approximate 30 degree angle with respect to horizontal, which results in a half-sitting position, which is the preferred position for pelvic exercise training.

Referring now to FIG. 1 and FIG. 15, the perineometer probe 10 is positioned within the vaginal cavity 12 for reacting pressure forces applied by pelvic muscle contractions. The lower wall 14 and the upper wall 16 of the vagina are connected to muscles, tissues, and nerves, that are indicated generally at 18, 20, and collectively referred to herein as the pubococcygeal and related perineal musculature. FIG. 1 also shows the uterus 22, which has an internal void known as the uterine body cavity 24, the cervix 26, the external os 28, which is the external opening of the cervix facing the vaginal cavity 12.

Other portions of the female anatomy shown in FIG. 1 include the bladder 30, ureter 32, the urethra 34, the labium minus 36, the labium majus 38, which join together in the region adjacent the clitoris 40, near the vaginal introitus 42, all clustered about the region generally known as the perineum 44.

Figure 2:
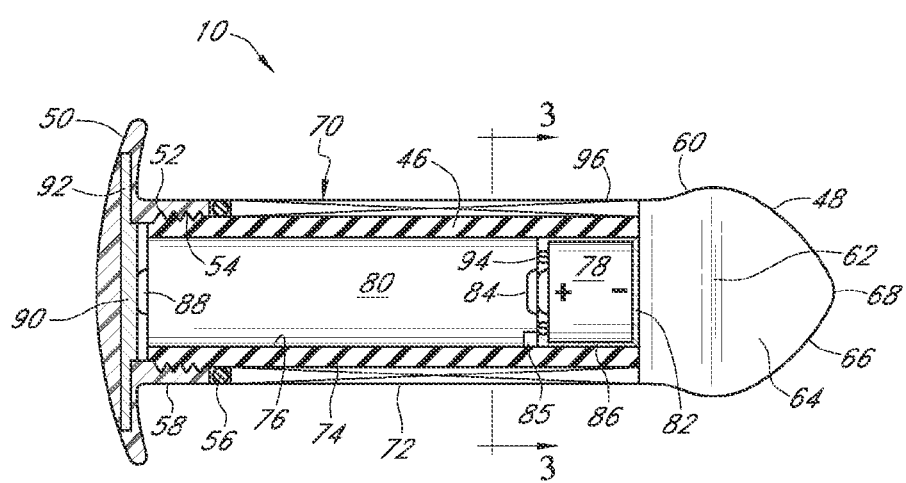
FIG. 2 is a side elevational view, partly in section, of the perineometer probe of the present invention.
Figure 4:
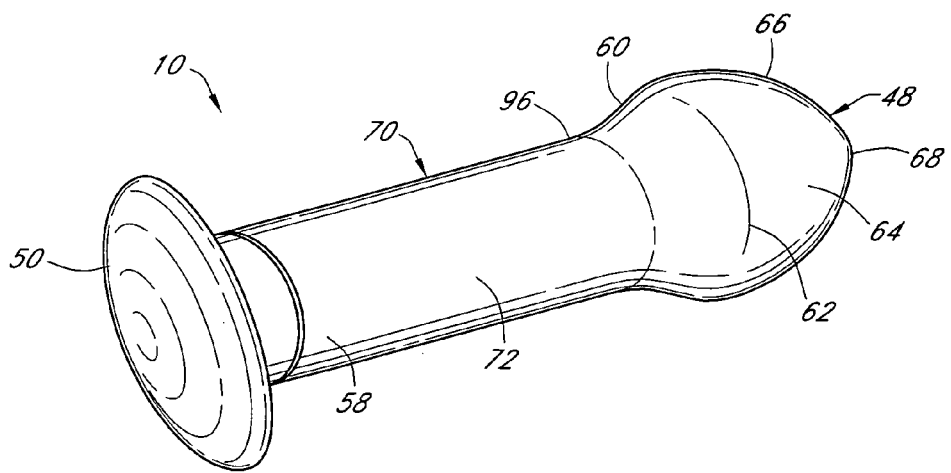
FIG. 4 is a perspective view of the perineometer probe of the present invention.

Referring now to FIG. 2 and FIG. 4, the perineometer probe 10 includes an elongated body portion or shaft 46 that is terminated on its distal end by a slightly enlarged and rounded head portion 48, and on its proximal end by a handle 50, which also functions as a closure cap. The handle 50 is fitted with threads 52 engaging mating threads 54 that are formed on the proximal end of the probe body. The interface between the handle and the probe body is sealed by an O-ring seal 56.

Figure 11:
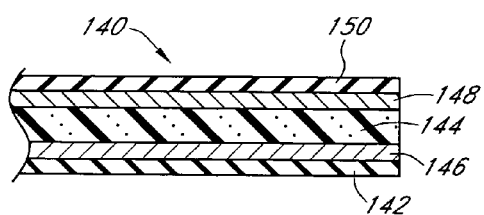
FIG. 11 is a sectional view of the flexible polymeric piezoelectric transducer sleeve, taken along the line 11-11 of FIG. 10.

As the patient is resting in the elevated lithotomy position shown in FIG. 11, the patient grasps the probe handle end 50 with her fingers. The patient then inserts the head portion 48 of the probe through the vaginal introitus 42 and into the vagina until the probe 10 is fully inserted, with the handle 50 engaging substantially flush against the labium minus 36. Upon full insertion, the probe head portion 48 extends into the vaginal cavity 12. The lower and upper vaginal walls 14, 16 close against the elongated body portion 46 to positively hold the probe 10 within the vaginal cavity.

The proximal end 58 of the elongated shaft portion 46 is adapted to seat at the introitus 42 of the vagina. The enlarged head portion 48 of the probe body is adapted to seat within the pelvic cavity 12. As shown in FIG. 4, the enlarged head portion 48 is characterized by a sloping retainer surface 60 that transitions smoothly from the shaft portion 46 along an outwardly flared, conical profile until it reaches an annular rim portion 62 at the limit of the outwardly flared profile. The enlarged head portion 48 then transitions smoothly from the annular rim portion 62 along a rounded portion 64 having an inwardly sloping surface 66 that forms a tapered profile. The tapered portion is terminated on the distal end by a rounded nose portion 68, which facilitates insertion.

Figure 3:
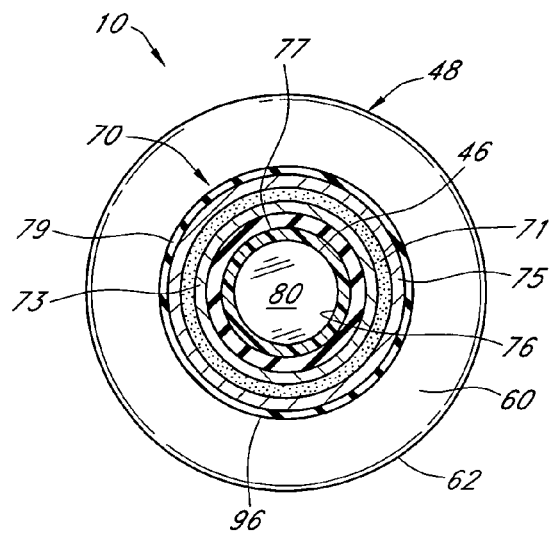
FIG. 3 is a sectional view of the perineometer probe, taken along the line 3-3 of FIG. 2.
Figure 2A:
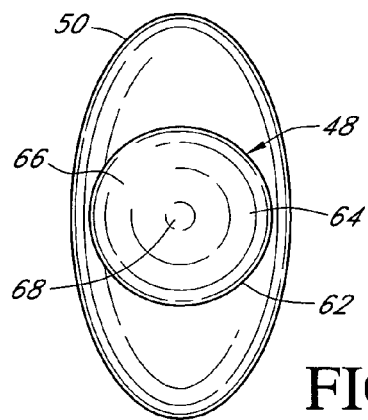
FIG. 2A is a front elevational view thereof.
Figure 5:
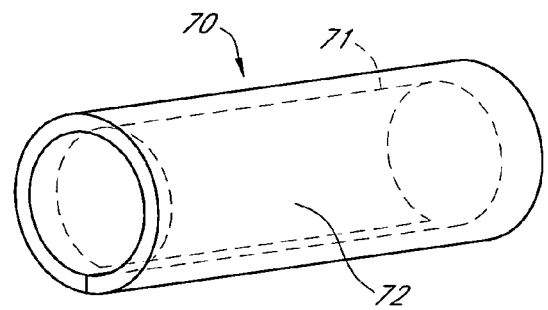
FIG. 5 is a perspective view of a transducer sleeve, shown removed from the perineometer probe.

According to the preferred embodiment, a pressure transducer sleeve 70 is fitted around the shaft portion 46 for sensing and providing an indication of pelvic muscle contraction pressure. As shown in FIG. 3 and FIG. 5, the transducer sleeve 70 contains a variable impedance element 71 capable of exhibiting a change in electrical impedance in response to changes in the amplitude of pressure forces applied to the transducer sleeve.

The variable impedance element 71 is distributed around and generally uniformly throughout a substantial portion of the sleeve and is sandwiched between first and second conductive electrodes 73, 75 which are disposed in electrical contact with the variable impedance element. Preferably, the conductive electrodes are formed by depositing metallization layers of a conductive metal, for example silver, on opposite side surfaces of the impedance element 71. A base layer 77 of a dielectric insulating material is applied to the external side surface of the first conductive electrode 73, and an outer layer 79 of a dielectric insulating material is applied to the external side surface of the second conductive electrode 75.

According to this probe configuration, when the pelvic floor muscles 18, 20 contract against the probe, the enlarged head portion 48 produces a differential contact zone of engagement in which the pressure forces of pelvic contraction are concentrated primarily along the externally facing contact surface 72 of the transducer sleeve 70. This clamping action creates a tight banding of pelvic muscle tissue around the transducer sleeve 10. The compressed muscle tissues 18, 20 engage against the flared retainer surface 60 of the head portion, which opposes expulsion of the probe from the vagina while a contraction is underway.

The shaft portion 46 is preferably in the form of a tubular sidewall 74 that surrounds an internal pocket 76. The distal end of the pocket 76 is sealed by the head portion 48 which forms the distal boundary of the pocket. A battery module 78, providing a supply potential, for example, of 6 volts DC, and a signal processor circuit module 80 are received in tandem alignment within the pocket 76.

A conductive DC supply input terminal 82 is mounted in the pocket between the probe head portion 48 for electrical contact engagement against the negative terminal (−) of the battery module. The distal end of the signal processor circuit module 80 is fitted with a conductive DC supply input terminal 84 for making electrical contact against the positive terminal (+) of the battery module 78. The distal end of the signal processor circuit module 80 is also fitted with a conductive DC supply input terminal 85 for connection to the negative supply input terminal 82. A conductive interconnect portion 86, connected to the negative supply input terminal 82, extends along the tubular sidewall 74 of the shaft 46 into electrical contact engagement against the negative supply input terminal 85 of the transmitter module 80.

The proximal end of the signal processor circuit module 80 is fitted with an RF output terminal 88 for making electrical contact against an antenna input terminal portion 90 of a dipole antenna 92 that is encapsulated within the handle 50. The RF output terminal 88 engages the antenna input terminal 90 and establishes firm electrical contact when the handle 50 is tightly sealed against the probe body 46. The electrical contact terminals are also brought into electrical contact engagement with the battery electrodes and complete a series electrical circuit when the handle 50 is tightly sealed against the probe body.

According to one aspect of the invention, ON/OFF control of the DC supply voltage is provided by a bias spring 94 acting in cooperation with the handle 50. The spring 94, preferably a Belville spring washer, is interposed between the DC battery module 78 and the signal processor circuit module 80 for urging the circuit module for movement away from electrical contact engagement with the positive terminal of the DC battery module. According with this arrangement, the handle 50 is disposed in threaded engagement with the shaft portion and engages against the circuit module 80 for moving the module axially through the pocket 76 against the bias force of the spring 94.

This spring bias action allows the DC voltage input terminal 84 of the transmitter module to be moved into and out of electrical contact engagement with the positive output terminal of the battery in response to clockwise and counter-clockwise rotation of the handle 50 relative to the shaft 46, thus making contact with the battery module and completing the DC supply circuit when the probe is activated ON, and breaking contact with the battery module and interrupting the DC supply circuit when the probe is turned OFF. The bias force of the spring 94 also maintains the RF signal output terminal 88 of the signal processor circuit module 80 in signal contact engagement with the RF signal input terminal 90 of the antenna 92 when the handle 50 is tightly sealed against the probe body.

The probe body 46, head portion 48 and handle 50 are fabricated from an injection moldable polymer material, preferably medical grade polymer resin that is a dielectric or electrically non-conductive, for example acrylic resin. The internal conductor terminals 82, 84, 86 and 90 are made of a flexible carbon impregnated conductive polymer composition which may be, for example silicone polymer. The external contact surfaces of the probe 10, including the transducer sleeve 70, are covered by a biologically inert coating layer 96 of a seamless medical grade silicone elastomer, which is preferred because of its high biocompatibility.

The silicone elastomer coating layer 96 transmits the pelvic pressure faithfully and its performance is temperature independent. Because the coating layer 96 is seamless and smooth, there are no joints or crevices to trap contaminants. Preferably, the coating layer 96 should be in the range of about ⅛ inch-³⁄₁₆ inch of a compressible elastomer material, which will allow shortening of the muscle fibers to induce muscle cell hypertrophy (increased muscle mass).

Figure 6:
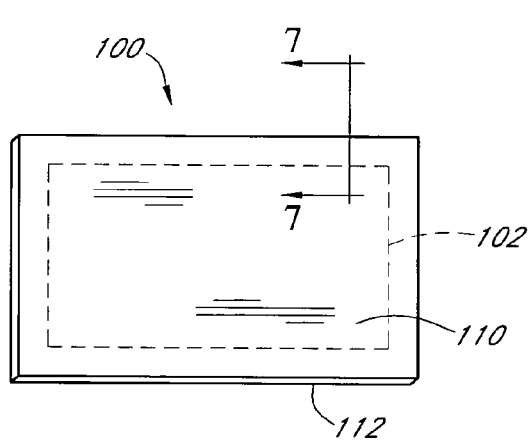
FIG. 6 is a developed plan view of a polymeric composition form transducer sleeve, shown in its flat configuration prior to assembly onto the perineometer probe.
Figure 7:
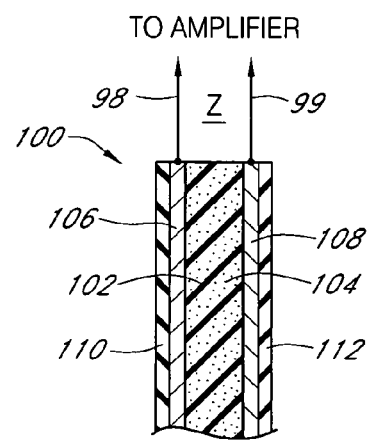
FIG. 7 is an enlarged sectional view of a portion of the polymeric composition transducer sleeve, taken along the line 7-7 of FIG. 6.

Referring now to FIG. 6 and FIG. 7, a variable impedance signal Z is conducted on signal conductors 98, 99 that are attached to the signal output nodes of a transducer 100. The impedance signal Z is proportional to pressure forces applied during contraction of the pelvic floor muscles 20, 22. This feedback signal is developed by a sensing body in which the variable impedance element is provided by commercially available transducer materials.

According to a first transducer embodiment, shown in FIG. 6 and FIG. 7, the sensing body of the transducer sleeve 100 is formed by a compressible body 102 of an insulating or weakly conductive polymer composition containing a dispersed matrix of particles 104 of at least one strongly conductive material selected from the group consisting of metals, alloys and reduced metal oxides, and first and second conductive electrodes 106, 108 disposed in electrical contact with the polymer composition. The conductive electrodes are covered by coating layers 110, 112 respectively, of a dielectric insulating polymer composition, preferably medical grade polymer resin that is a dielectric or electrically non-conductive, for example acrylic resin.

Figure 8:
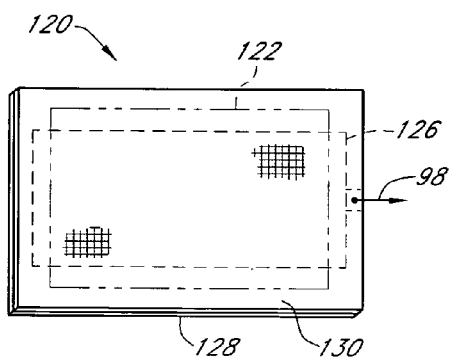
FIG. 8 is a developed plan view of a textile form fabric transducer sleeve, shown in its flat configuration prior to assembly onto the perineometer probe.
Figure 9:
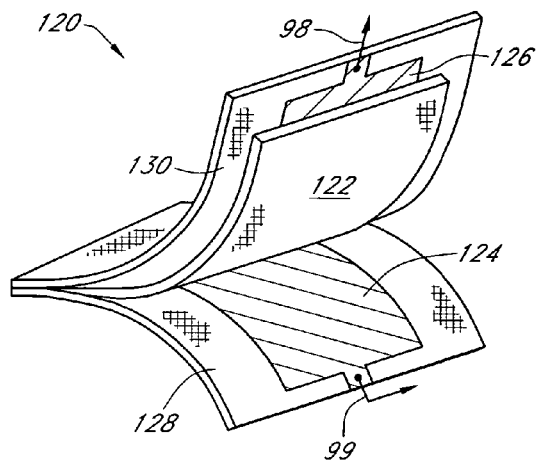
FIG. 9 is a peeled-away perspective view of the textile form fabric transducer sleeve of FIG. 8.

According to another transducer embodiment, shown in FIG. 8 and FIG. 9, the sensing body of a pressure transducer 120 is provided by a textile form variable resistance element 122 interleaved with textile form conductive members 124, 126. The variable resistance element and conductive members are enclosed between textile form non-conductive base and covering layers 128, 130. The textile layers are formed of woven nylon or polyester yarns. The conductive members are formed by printing the facing surfaces of the covering layers 128, 130 with deposits of conductive inks or polymer pastes containing metals, metal oxides or semi-conductive materials such as conductive polymers or carbon.

Preferably, the variable impedance element 122 exhibits quantum tunneling conductance when deformed. This is a well known property of polymer compositions in which a filler selected from powder-form metals or alloys, electrically conductive oxides of such elements and alloys, and admixtures thereof with a non-conductive elastomer. The filler is dispersed within the elastomer and remains structurally intact and the voids present in the starting filler powder become infilled with elastomer and particles of filler become set in close proximity during curing of the elastomer.

Figure 10:
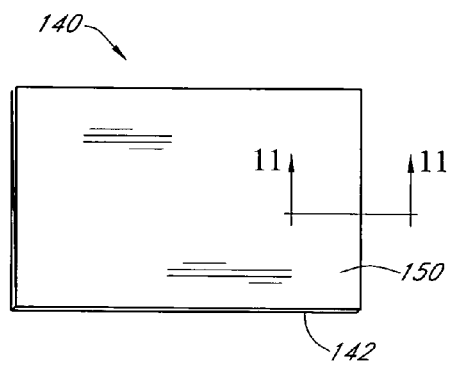
FIG. 10 is a developed plan view of a flexible polymeric piezoelectric form transducer sleeve, shown in its flat configuration prior to assembly onto the perineometer probe.

According to yet another embodiment, shown in FIG. 10 and FIG. 11, the sensing body of a pressure transducer 140 is a multi-layer flexible laminate comprising a base contact layer 142 of a flexible, non-conductive sheet material, for example, Mylar™ polyester film, a middle polymeric piezoelectric sheet 144 having moralized coating layers 146 and 148 on either side thereof, and an outer contact layer 150 of a flexible sheet material, for example, Mylar™ polyester film.

Preferably, the polymeric piezoelectric sheet 144 is a film of polyvinylidene fluoride (PVDF), a fluoroplastic resin that is commercially available as pellets for extrusion and molding. PVDF film is known to possess piezoelectric characteristics in its beta phase. Beta-phase PVDF is produced from ultra pure film by stretching it during extrusion. Both surfaces of the film extrusion are then moralized, and the film is subjected to a high voltage to polarize its atomic structure. When compressed or stretched, the polarized PVDF film generates a voltage across the moralized surfaces, in proportion to the induced strain.

The electrical equivalent or characteristic impedance Z of the piezoelectric film element 144 is a voltage source in series with a capacitance. The voltage source is the piezoelectric generator itself, and this source is directly proportional to the applied stimulus (pressure or strain). The transducer output voltage will absolutely follow the applied pressure, and the output voltage is then buffered, filtered and scaled in the signal processor module 80 before it is converted to a digital data feedback signal.

The polyester film layers 142 and 150 are adhesively attached to the metallized coating layers 146, 148 respectively. Additionally, the base layer 142 is adhesively bonded to the probe shaft 46. The piezoelectric material 144 is preferably a layer of polarized polyvinylidene fluoride (PVDF) film sandwiched between the moralized coating layers 146, 148 of electrically conductive metal. Preferably, the polymeric piezoelectric sheet 144 is approximately 28 microns in thickness, and the metallized coating layers 146, 148 are silver deposits of about 0.1 microns in thickness.

Referring again to FIGS. 4 and 5, the pressure transducer is formed by rolling a rectangular swatch of one of the transducer embodiments 100, 120 or 140 described above to produce a tubular sleeve 70 having an annular transducer body. The transducer swatch is provided in a length dimension approximately equal to the load surface length L of the probe and a width W approximately equal to the O.D. circumference of the tubular shaft sidewall 74. The transducer swatch is then rolled and adhesively bonded onto the tubular housing 64. Alternatively, the transducer swatch is rolled into tubular sleeve form, forming an annular body 70 as indicated in FIG. 5, and the proximal end of the probe is then inserted into the sleeve and sealed. Optionally, the transducer sleeve 70 can be molded onto the tubular sidewall 64 where a polymeric transducer material is selected.

The transducer sleeve 70 has an extended pressure-responsive area 72 that is substantially coextensive in length with the run of the pelvic floor muscles 18, 20. Consequently, when the probe 10 is fully inserted with the handle 50 engaging the labium majus 38, the pressure responsive area will span the pelvic floor muscles of most adult women.

Preferably, the transducer sleeve 70 is attached to the probe sidewall 46 by an adhesive deposit. Excellent coupling is obtained through adhesive attachment using pressure sensitive adhesive supplied by 3M Corporation, such as Product No. Y-9485. The adhesively coupled transducer sleeve 70 provides high transducer sensitivity, low mechanical and acoustic impedance to produce accurate transducer output signals throughout a broad range of loadings. The flexible transducer sleeve 70 provides a linear voltage output for a given force, enabling the sensing of movements as low as respiration and pulse. Moreover, because of the toughness and flexibility of the polymeric materials, the transducer sleeve 70 is resistant to breakage caused by rough handling.

As indicated in FIG. 12, the tubular shaft 46 serves as a reaction core member that supports the transducer sleeve 70 and reacts compression loading applied during contractions of the pelvic floor muscles 18, 20. As the pelvic floor muscles contract, the transducer sleeve 70 is stressed in accordance with changes in applied loading and yields a variable impedance output signal Z in accordance with the changes, while the support shaft 46 reacts the compression forces and provides tactile sensory feedback directly to the patient.

Referring now to FIG. 12, the variable impedance signal Z is input to the signal processor circuit module 80 via conductors 98, 99 that are electrically connected to the metallization deposit layers of the transducer. The signal processor circuit module 80 includes a low noise amplifier 160, an analog-to-digital converter (ADC) 162, and an RF transmitter 164. The analog impedance signal Z from the transducer sleeve 70 is first buffered, filtered and amplified by the low noise amplifier 160, and then converted to a digital data signal by the analog-to-digital converter (ADC) 162. Preferably, the components of the signal processor circuit module 80 are implemented by conventional RF integrated circuit (RFIC) technology.

The digitized feedback signal is input to the RF transmitter 164 which is operable in the 433 MHz band which is dedicated for scientific and medical purposes, at 25 milliwatts nominal output. Under this arrangement, the transmitted signal has an effective range of about 2 meters, which provides sufficient signal strength for reliable reception by a hand-held monitor.

Referring now to FIG. 13 and FIG. 14, a hand-held monitor 170 includes an RF receiver 174 that receives a wireless feedback signal 176 via an internal antenna 178. The wireless feedback signals are fed into a display driver 180 that provides feedback data signals 182 to an audio and visual indicator 184. The indicator provides a visual graphic presentation of a pelvic contraction, for example the waveform 186, and audio output signals in response to pelvic contractions.

The monitor 170 may also be configured to display other data, such as intravaginal temperature, for example, 98.4° F.; the elapsed time of pelvic contraction, for example E 5 (5 seconds); and the numerical pressure tension value of the contraction strength in cm water, for example P10 (10 cm water). Negative values of pelvic tension pressure (relative to the nominal "at rest" pelvic tension level) can also be displayed when the probe is used to monitor relaxation training exercises for treatment of pelvic muscle spasm disorders. Preferably, the displayed pressure tension value and the waveform are updated ten times per second or more during contractions.

The visual display presentation is implemented by a conventional liquid crystal display screen 188, preferably with backlighting. A piezoelectric speaker 190 and a headphone jack 192 provide audio output. Controls are provided for power on-off function (switch 194), display reset (switch 196), volume control function (dial 198) and pressure calibration (normalize pressure display to read zero for "at rest" pelvic pressure level—switch 200).

In the above described embodiments, ultra-low power radio frequency (RF) transmission is preferred for wireless high speed data transmission to the receiver 174. One-way or two-way wireless data communication links may be implemented. Any short range, wireless RF data communication protocol, for example Bluetooth, Wi-Fi or Zigbee, may be used for this purpose.

Optionally, the probe 10 can be fitted with a thermal transducer for sensing and providing an indication of pelvic temperature, for example for monitoring the onset of ovulation. Although the probe is sealed by a removable handle in the exemplary embodiments, the probe and handle can be hermetically sealed if desired.

Alternative embodiments of the transducer sleeve are shown in FIGS. 16-23. These transducer sleeves each include one or more discrete transducer elements that are interconnected and embedded or enclosed in an annular sleeve body. In each sleeve embodiment, the impedance element of the transducer strips is constructed with a selected one of the conventional transducer materials described above.

Referring to FIG. 16 and FIG. 17, a transducer sleeve 210 includes multiple discrete transducer strips 212, 214, 216 and 218 embedded or enclosed within a flexible body 220 of a compressible polymer composition, for example a closed cell polymer foam resin. The transducer strips extend along the length of the probe shaft, and are evenly spaced around the circumference of the shaft. The impedance elements are interconnected in parallel circuit relation, collectively providing a common impedance output signal Z.

Referring to FIG. 18 and FIG. 19, a transducer sleeve 230 includes multiple discrete transducer bands 232, 234, 236, 238 and 240 embedded or enclosed within a flexible body 242 of a compressible polymer composition, for example a closed cell polymer foam resin. The transducer bands encircle the probe shaft, and are evenly spaced along the length of the shaft. The impedance elements are interconnected in parallel circuit relation, providing a common impedance output signal Z.

Figure 20:
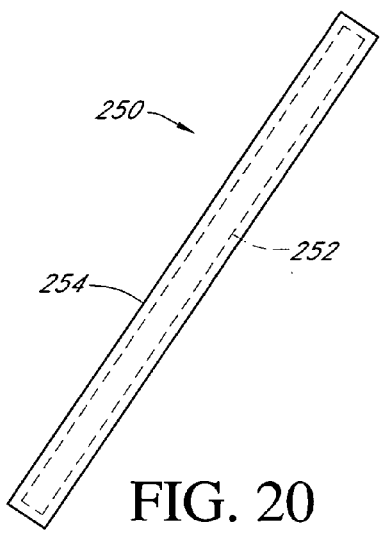
FIG. 20 is a developed plan view of a transducer sleeve with a spiral wrap transducer element, shown in its flat configuration prior to assembly onto the perineometer probe.
Figure 21:
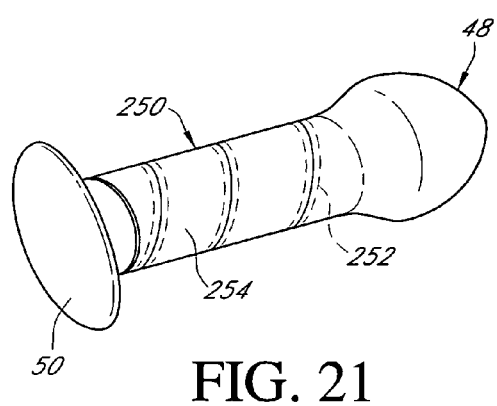
FIG. 21 is a perspective view of the spiral wrap form transducer sleeve shown assembled onto a probe.

Referring to FIG. 20 and FIG. 21, a transducer sleeve 250 includes a single elongated transducer strip 252 embedded or enclosed within a flexible body 254 of a compressible polymer composition, for example closed cell polymer foam resin. The transducer strip is wrapped around the probe shaft in a spiral pattern, and is secured thereto by an adhesive deposit. The impedance element is a continuous strip or body of a selected one of the conventional transducer materials described above.

Figure 22:
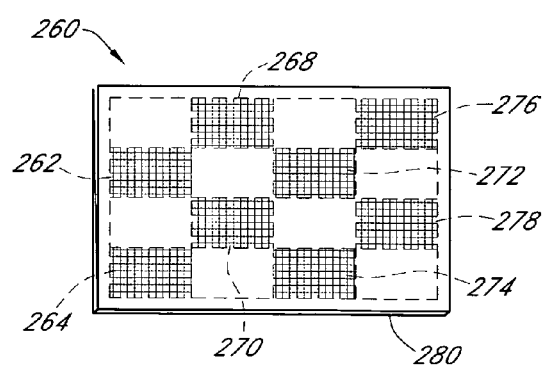
FIG. 22 is a developed plan view of a transducer sleeve with multiple transducer elements arranged in a grid pattern, shown in its flat configuration prior to assembly onto the perineometer probe.
Figure 23:
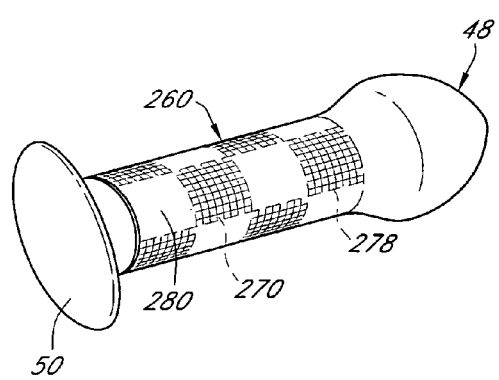
FIG. 23 is a perspective view of the grid form transducer sleeve shown assembled onto a probe.
Figure 24:
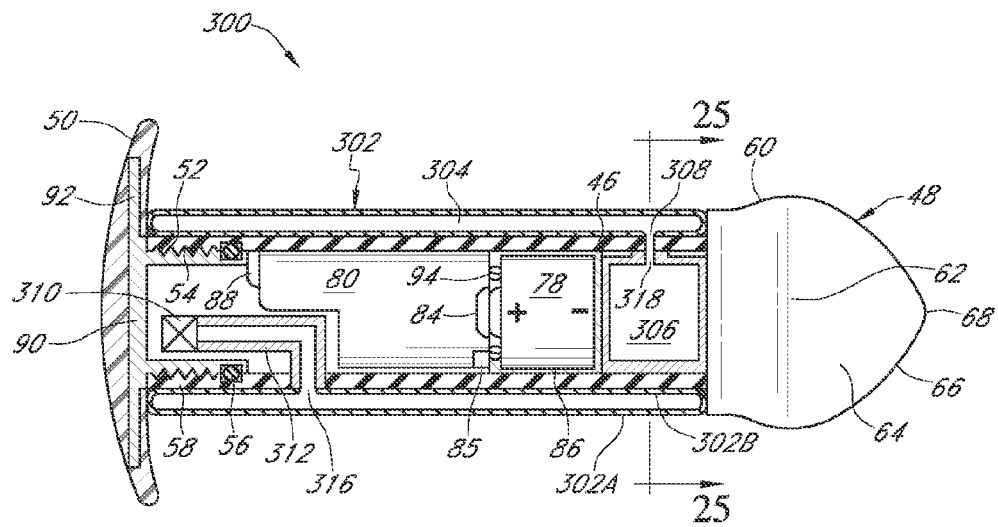
FIG. 24 is a side elevational view, partly in section, of a wireless perineometer probe having an inflatable transducer sleeve according to an alternative embodiment of the present invention.
Figure 25:
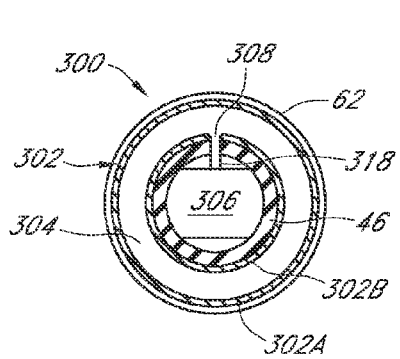
FIG. 25 is a sectional view thereof, taken along the line 25-25 of FIG. 24.

Referring to FIG. 22 and FIG. 23, a transducer sleeve 260 includes multiple discrete transducer patches 262, 264, 268, 270, 274, 276, 278, and 280 arranged in a checker board pattern and embedded or enclosed within a flexible body 272 of a compressible polymer composition, for example closed cell polymer foam resin. The transducer patches are evenly spaced apart in a rectangular grid array throughout the sleeve body. The impedance elements of the patches are interconnected in parallel circuit relation, providing a common impedance output signal Z.

An alternative wireless perineometer probe 300 is shown in FIGS. 24-27. In this embodiment, an air bladder 302 senses pelvic contraction pressure. The air bladder 302 is in the form of an elongated, annular sleeve having an outer sidewall 302A and an inner sidewall 302B separated by an annular air pressure chamber 304. The air bladder 302 is fitted around and attached to the shaft 46, preferably by an adhesive deposit, and is coupled in fluid communication with a pressure transducer module 306 via an inlet port 308 that intersects the shaft sidewall 46. Although a double-walled bladder is illustrated, a single-wall bladder, hermetically sealed around the shaft 46 on its proximal and distal ends, can be substituted. Various medical grade rubber materials can be used to fabricate the bladder. Preferably, the bladder is fabricated of a seamless, medical grade, low-modulus, non-latex, soft nitrile composition, having a sidewall thickness in the range of 4 mils-6 mils.

Figure 27:
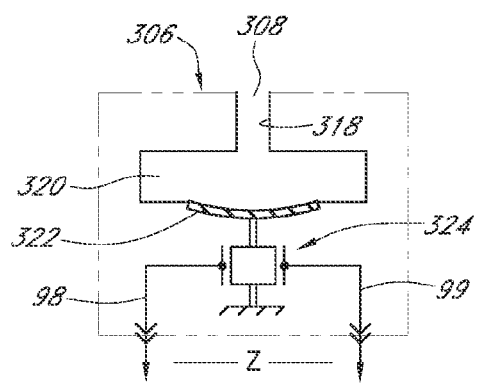
FIG. 27 is a circuit diagram of a piezoelectric transducer contained in the transducer module of FIG. 24.
Figure 26:
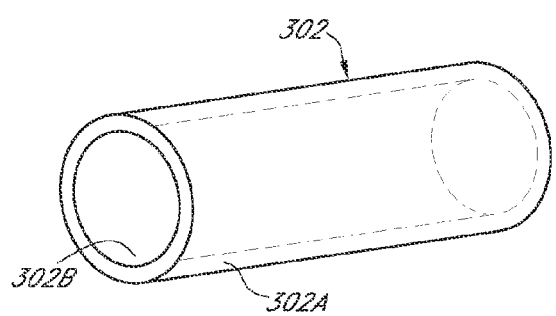
FIG. 26 is a perspective view of the inflatable transducer sleeve shown in FIG. 24.

The air bladder 302 is pressurized through a check valve 310 and fill tube 312 that are coupled in fluid communication with the annular bladder chamber 304 via an inlet port 316 that is formed through the shaft sidewall 46. Access to the check valve is provided by removing the handle 50, and the bladder chamber is pressurized manually by a small hand pump. The internal bladder pressure is communicated to the transducer module 306 via a flow passage 318 that is connected in fluid communication with an internal bellows chamber 320 disposed within the transducer module 306, as shown in FIG. 27.

A resilient membrane 322, attached across the bellows chamber, is mechanically coupled to a piezoelectric crystal transducer 324. As the membrane 322 deflects and extends, it applies mechanical stress across the crystal in proportion to the magnitude of the air pressure in the bellows chamber. The electrical impedance Z of the piezoelectric crystal transducer changes in proportion to the applied pressure, and this impedance signal is input to the transmitter module 80 via the signal conductors 98, 99. The piezoelectric crystal transducer 324 is preferably comprises natural, reprocessed crystalline quartz with a long discharge time constant operable in the charge mode as a dynamic pressures sensor.

The electrical equivalent or characteristic impedance Z of the piezoelectric crystal 324 is a voltage sources in series with a capacitance. The voltage source is the piezoelectric generator itself, and the source is directly proportional to the applied stimulus (pressure or strain). The transducer output voltage will follow the applied pressure, and the output voltage is the buffered, filtered and scaled in the signal processor module 80 before it is converted to a digital data feedback signal. After being scaled and digitized, the pelvic contraction pressure signals are transmitted as wireless RF signals to the hand-held monitor 170, as indicated in FIG. 15.

We claim:

1. A probe receivable within a pelvic cavity for sensing contraction pressure applied by pelvic floor muscles, comprising:
   an elongated shaft having an external surface portion;
   a transducer including a distributed sensing arrangement provided by a sensing body extending lengthwise and circumferentially in overlapping relation along the external surface portion of the shaft;
   the sensing body including a plurality of variable impedance elements capable of exhibiting a change in electrical impedance in response to pelvic floor muscle contractions against the sensing body, the variable impedance elements being distributed around and lengthwise along a portion of the sensing body;
   a dielectric insulating material forming a portion of the sensing body and being disposed between the pelvic cavity and the plurality of variable impedance elements, such that the variable impedance elements are disposed at an external surface of the sensing body; and
   a signal processor circuit disposed in the probe and electrically coupled to the variable impedance elements for producing a feedback signal in response to the electrical impedance exhibited by the variable impedance elements.

2. A probe according to claim 1, wherein the sensing body comprises an annular sleeve mounted around the sidewall surface portion, and the variable impedance elements are substantially coextensive in surface area with the annular sleeve.

3. A probe according to claim 1, wherein the variable impedance elements comprise a polymer composition that exhibits quantum tunneling conductance when deformed.

4. A probe according to claim 1, wherein the sensing body comprises a multi-layer, flexible laminate of a first layer of a dielectric or non-conductive sheet material, a second layer of dielectric or non-conductive sheet material, and intermediate layer of a polymeric piezoelectric material having metallized conductive coating layers on either side thereof disposed between the first and second non-conductive layers.

5. A probe according to claim 1, the probe comprising distal shaft portion having an enlarged head portion adapted to seat within a pelvic cavity and having a proximal shaft portion adapted for seating at the introitus of the pelvic cavity, and the sensing body is disposed intermediate to the proximal shaft portion and the head portion.

6. A probe according to claim 1, wherein the shaft has an external reaction surface for reacting compression forces applied by pelvic muscle contractions, and the sensing body is substantially coextensive in length and overlaps a substantial portion of the shaft reaction surface.

7. A probe according to claim 1, wherein the probe comprises:
   a probe body having a head portion adapted to seat within a pelvic cavity and a handle extending from the shaft to enable the probe body to be manually inserted into and withdrawn from the pelvic cavity; and
   the sensing body is fitted in overlapping relation about the shaft intermediate the handle and head portion.

8. A probe according to claim 1, the probe comprising:
   a probe body having an enlarged head portion adapted to seat within a pelvic cavity and having a shaft portion attached to the head portion and adapted to seat at the introitus of the pelvic cavity, wherein the enlarged head portion is characterized by a first surface that transitions from the shaft portion along an outwardly flared profile to a rim, and by a second surface that transitions from the rim along an inwardly tapered profile.

9. A probe according to claim 1, wherein:
   the shaft is intersected by a longitudinal pocket; and
   the signal processor circuit is contained within the longitudinal pocket.

10. A probe according to claim 1, wherein the probe comprises a handle portion and a head portion, and the shaft portion is disposed between the handle portion and the head portion.

11. A probe according to claim 1, wherein the signal processor circuit comprising:
    a wireless RF transmitter assembly contained within the probe; and
    a DC battery is contained within the probe for supplying electrical operating current to the wireless RF transmitter.

12. A probe according to claim 1, wherein the probe comprises a handle portion attached to the shaft;
    the shaft is intersected by a pocket and a wireless RF transmitter module is disposed within the pocket;
    a DC battery is disposed within the pocket for electrical contact engagement with the transmitter module;
    a spring is interposed between the DC battery and the transmitter module for urging the transmitter module for movement away from electrical contact engagement with the DC battery; and
    the handle is disposed in threaded engagement with the shaft and is engagable with the transmitter module for moving the transmitter module axially through the pocket against the bias of the spring and thereby moving the transmitter module into and out of electrical contact engagement with the battery in response to clockwise and counter-clockwise rotation of the handle relative to the shaft, respectively.

13. A probe according to claim 1, wherein:

the probe comprises a handle portion attached to the shaft;

the shaft is intersected by a pocket and a wireless RF transmitter module is disposed within the pocket, the transmitter module including an RF signal output terminal;

an antenna is disposed on the handle portion, and the antenna includes an RF signal input terminal;

a spring is interposed between the shaft and the transmitter module for urging the transmitter module for axial movement through the pocket into electrical contact engagement with the RF signal input terminal; and the handle is disposed in threaded engagement with the shaft and is engagable with the transmitter module for moving the transmitter module axially through the pocket against the bias of the spring in response to rotation of the handle relative to the shaft and thereby maintaining the RF signal output terminal of the transmitter module in signal contact engagement with the RF signal input terminal of the antenna.

14. A probe receivable within a pelvic cavity for sensing contraction pressure applied by pelvic floor muscles against the probe, comprising:

a shaft that is intersected by a pocket;

a transducer sleeve extending circumferentially and lengthwise in overlapping relation around and along the shaft, the transducer sleeve including a variable impedance element capable of exhibiting a change in electrical impedance in response to pressure forces applied to the transducer sleeve, the variable impedance element being distributed around and lengthwise through the transducer sleeve to provide a distributed sensing arrangement;

a dielectric insulating material associated with the transducer sleeve, the dielectric insulating material disposed between the pelvic cavity and the variable impedance element such that the variable impedance element is disposed at an external surface of the transducer sleeve; and an electronic circuit module disposed in the pocket and electrically coupled to the variable impedance element for transmitting wireless feedback signals in response to pelvic contraction forces applied to the transducer sleeve.

15. A probe receivable within a pelvic cavity for sensing contraction pressure applied by pelvic floor muscles against the probe, comprising:

a probe body having a head portion adapted to seat within a pelvic cavity and having a shaft portion adapted to seat at the introitus of the pelvic cavity;

the shaft portion having a pocket for receiving an electronic circuit module and a DC battery for supplying DC operating power;

a transducer sleeve extending circumferentially and lengthwise in overlapping relation around and along the shaft portion intermediate the closure cap and the head portion, the transducer sleeve including a variable impedance element capable of exhibiting a change in electrical impedance in response to pelvic contraction forces applied to the transducer sleeve, the variable impedance element being distributed around and lengthwise through the transducer sleeve to provide a distributed sensing arrangement;

a dielectric insulating material associated with the transducer sleeve, the dielectric insulating material disposed between the pelvic cavity and the variable impedance element such that the variable impedance element is disposed at an external surface of the transducer sleeve; and an electronic circuit module enclosed within the pocket and electrically coupled to the variable impedance element, the electronic circuit module including an RF transmitter for transmitting wireless feedback signals in response to contraction forces applied to the transducer sleeve.

16. Apparatus for training a patient's pelvic floor muscles, comprising in combination:

a probe receivable within a patient's pelvic cavity for engaging pelvic floor muscles, the probe including a shaft and a sensing transducer extending lengthwise and circumferentially in overlapping relation along the shaft, and the sensing transducer including a variable impedance element capable of exhibiting a change in electrical impedance in response to pelvic floor muscle contractions applied against the sensing transducer, the variable impedance element being distributed around and lengthwise through the transducer sleeve to provide a distributed sensing arrangement;

a dielectric insulating material associated with the transducer sleeve, the dielectric insulating material disposed between the pelvic cavity and the variable impedance element such that the variable impedance element is disposed at an external surface of the transducer sleeve;

a signal processor circuit contained in the probe and electrically coupled to the sensing transducer for transmitting a wireless radio frequency signal containing feedback information related to the electrical impedance of the transducer; and a portable monitor including a radio frequency receiver for receiving the wireless signal and an indicator device coupled to the receiver for producing a feedback signal in response to information contained in the wireless signal and in a format that can be observed or heard by a patient while a training exercise is underway.

17. Apparatus for exercising and training a patient's pelvic floor muscles according to claim 16, the indicator display device including:

visual display apparatus for displaying an alphanumeric data representation of feedback information contained in the wireless signal.

18. Apparatus for exercising and training a patient's pelvic floor muscles according to claim 16, the indicator display device including:

visual display apparatus for displaying a visual graphic representation of feedback information contained in the wireless signal.

19. Apparatus for exercising and training a patient's pelvic floor muscles according to claim 16, the indicator device including:

audio reproduction apparatus for sounding an audible signal that corresponds to feedback information contained in the wireless signal.

20. A probe according to claim 1, wherein the variable impedance elements comprise a quantum tunneling composition.

* * * * *